(12) United States Patent
Brannan

(10) Patent No.: US 9,625,395 B2
(45) Date of Patent: Apr. 18, 2017

(54) MICROWAVE ABLATION ANTENNA RADIATION DETECTOR

(71) Applicant: COVIDIEN LP, Mansfield, MA (US)

(72) Inventor: Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 214 days.

(21) Appl. No.: 14/499,937

(22) Filed: Sep. 29, 2014

(65) Prior Publication Data

US 2015/0015237 A1 Jan. 15, 2015

Related U.S. Application Data

(63) Continuation of application No. 14/048,835, filed on Oct. 8, 2013, now Pat. No. 8,847,830, which is a continuation of application No. 12/487,917, filed on Jun. 19, 2009, now Pat. No. 8,552,915.

(51) Int. Cl.

| | |
|---|---|
| *G08B 23/00* | (2006.01) |
| *G01S 3/02* | (2006.01) |
| *G01N 22/00* | (2006.01) |
| *A61B 18/14* | (2006.01) |
| *A61B 18/18* | (2006.01) |
| *G01R 29/08* | (2006.01) |
| *H01Q 1/24* | (2006.01) |
| *G01R 21/00* | (2006.01) |
| *A61B 17/00* | (2006.01) |

(52) U.S. Cl.
CPC ......... *G01N 22/00* (2013.01); *A61B 18/1492* (2013.01); *A61B 18/1815* (2013.01); *G01R 21/00* (2013.01); *G01R 29/0878* (2013.01); *H01Q 1/248* (2013.01); *A61B 2017/00039* (2013.01)

(58) Field of Classification Search
CPC G01N 22/00; A61B 18/1492; A61B 18/1815; G01R 21/00; G01R 29/0878
USPC ............ 324/76.14; 340/573.1, 600; 600/424, 600/430; 343/703, 841
See application file for complete search history.

(56) References Cited

U.S. PATENT DOCUMENTS

| | | |
|---|---|---|
| 3,631,363 A | 12/1971 | Miller |
| D223,367 S | 4/1972 | Kountz |
| 4,215,275 A | 7/1980 | Wickersheim |
| D263,020 S | 2/1982 | Rau, III |

(Continued)

FOREIGN PATENT DOCUMENTS

| | | |
|---|---|---|
| CN | 1103807 A | 6/1995 |
| DE | 390937 C | 3/1924 |

(Continued)

OTHER PUBLICATIONS

Esterline Product Literature, "Light Key: Visualize a Virtual Keyboard. One With No Moving Parts", Nov. 1, 2003; 4 pages.

(Continued)

*Primary Examiner* — Eric M Blount

(57) ABSTRACT

A radiation detector disposed on a microwave antenna assembly is disclosed. The radiation detector includes a receiving antenna adapted to receive errant microwave energy and a rectifier coupled to the receiving antenna that is adapted to rectify at least a portion of the errant microwave energy. A filter is coupled to the rectifier and is adapted to convert the rectified microwave energy into a detection signal.

11 Claims, 11 Drawing Sheets

(56) References Cited

U.S. PATENT DOCUMENTS

| | | | |
|---|---|---|---|
| D266,842 S | 11/1982 | Villers et al. |
| 4,397,313 A | 8/1983 | Vaguine |
| 4,448,547 A | 5/1984 | Wickersheim |
| 4,462,412 A | 7/1984 | Turner |
| D278,306 S | 4/1985 | McIntosh |
| 4,539,567 A | 9/1985 | Brewer |
| 4,560,286 A | 12/1985 | Wickersheim |
| 4,572,190 A | 2/1986 | Azam et al. |
| 4,580,557 A | 4/1986 | Hertzmann |
| D295,893 S | 5/1988 | Sharkany et al. |
| D295,894 S | 5/1988 | Sharkany et al. |
| 4,753,248 A | 6/1988 | Engler et al. |
| 4,798,215 A | 1/1989 | Turner |
| 5,097,844 A | 3/1992 | Turner |
| 5,350,391 A | 9/1994 | Iacovelli |
| 5,375,596 A * | 12/1994 | Twiss .............. A61B 5/06 128/903 |
| D354,218 S | 1/1995 | Van de Peer |
| 5,417,210 A | 5/1995 | Funda et al. |
| 5,429,133 A | 7/1995 | Thurston et al. |
| 5,671,133 A | 9/1997 | Fujita et al. |
| 6,031,375 A | 2/2000 | Atalar et al. |
| D424,693 S | 5/2000 | Pruter |
| D424,694 S | 5/2000 | Tetzlaff et al. |
| D425,201 S | 5/2000 | Tetzlaff et al. |
| 6,222,193 B1 | 4/2001 | Thurston et al. |
| D449,886 S | 10/2001 | Tetzlaff et al. |
| 6,332,089 B1 | 12/2001 | Acker et al. |
| 6,375,606 B1 | 4/2002 | Garibaldi et al. |
| D457,958 S | 5/2002 | Dycus et al. |
| D457,959 S | 5/2002 | Tetzlaff et al. |
| 6,424,869 B1 | 7/2002 | Carr et al. |
| 6,603,994 B2 | 8/2003 | Wallace et al. |
| D487,039 S | 2/2004 | Webster et al. |
| 6,725,080 B2 | 4/2004 | Melkent et al. |
| D496,997 S | 10/2004 | Dycus et al. |
| D499,181 S | 11/2004 | Dycus et al. |
| 7,025,765 B2 | 4/2006 | Balbierz et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al |
| D564,662 S | 3/2008 | Moses et al. |
| D576,932 S | 9/2008 | Strehler |
| 7,439,736 B2 | 10/2008 | Meaney et al. |
| 7,467,015 B2 | 12/2008 | van der Weide |
| D594,736 S | 6/2009 | Esjunin |
| D594,737 S | 6/2009 | Kelly et al. |
| 7,565,207 B2 | 7/2009 | Turner et al. |
| D606,203 S | 12/2009 | Husheer et al. |
| D613,412 S | 4/2010 | DeCarlo |
| D634,010 S | 3/2011 | DeCarlo |
| D681,810 S | 5/2013 | DeCarlo |
| 8,552,915 B2 | 10/2013 | Brannan |
| 8,847,830 B2 | 9/2014 | Brannan |
| 2002/0022836 A1 | 2/2002 | Goble et al. |
| 2002/0075189 A1* | 6/2002 | Carillo, Jr. ............. H01Q 1/245 343/702 |
| 2002/0087079 A1 | 7/2002 | Kaufman et al. |
| 2004/0097805 A1 | 5/2004 | Verard et al. |
| 2004/0242992 A1 | 12/2004 | Hareyama |
| 2005/0038419 A9 | 2/2005 | Arnold et al. |
| 2005/0082368 A1* | 4/2005 | Watanabe .............. H01Q 1/06 235/451 |
| 2007/0191825 A1 | 8/2007 | Cronin et al. |
| 2009/0125020 A1 | 5/2009 | Douglass et al. |
| 2011/0021888 A1 | 1/2011 | Sing et al. |
| 2011/0270241 A1 | 11/2011 | Boutoussov |
| 2013/0034553 A1 | 2/2013 | Fandl et al. |
| 2013/0241769 A1 | 9/2013 | Brannan et al. |
| 2013/0245624 A1 | 9/2013 | Bahney |
| 2013/0253500 A1 | 9/2013 | Lee et al. |
| 2013/0261617 A1 | 10/2013 | Podhajsky |
| 2013/0261620 A1 | 10/2013 | Brannan et al. |
| 2013/0267946 A1 | 10/2013 | Brannan et al. |
| 2013/0289560 A1 | 10/2013 | DeCarlo et al. |
| 2013/0304057 A1 | 11/2013 | Rossetto |
| 2013/0317407 A1 | 11/2013 | Reid, Jr. et al. |
| 2013/0317495 A1 | 11/2013 | Brannan |
| 2013/0324910 A1 | 12/2013 | Ohri et al. |
| 2013/0324911 A1 | 12/2013 | Ohri et al. |
| 2013/0338661 A1 | 12/2013 | Behnke, II |
| 2013/0345541 A1 | 12/2013 | Nau, Jr. |
| 2013/0345551 A1 | 12/2013 | Arts et al. |
| 2013/0345552 A1 | 12/2013 | Arts et al. |
| 2013/0345699 A1 | 12/2013 | Brannan et al. |
| 2014/0000098 A1 | 1/2014 | Dunning et al. |
| 2014/0005655 A1 | 1/2014 | Brannan |
| 2014/0005657 A1 | 1/2014 | Brannan et al. |
| 2014/0018668 A1 | 1/2014 | Zheng et al. |
| 2014/0018677 A1 | 1/2014 | Sharonov |
| 2014/0018793 A1 | 1/2014 | Sharonov |
| 2014/0094789 A1 | 4/2014 | Brannan |
| 2014/0094792 A1 | 4/2014 | Sharonov |
| 2014/0094793 A1 | 4/2014 | Sharonov |
| 2014/0094794 A1 | 4/2014 | Orszulak |
| 2014/0094797 A1 | 4/2014 | Brannan |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |
| EP | 0 481 685 A1 | 4/1992 |
| EP | 0 521 264 A2 | 1/1993 |
| EP | 0 556 705 A1 | 8/1993 |
| EP | 0 558 429 A1 | 9/1993 |
| EP | 0572131 A1 | 12/1993 |
| EP | 0 648 515 A1 | 4/1995 |
| EP | 0541930 B1 | 3/1998 |
| EP | 0 836 868 A2 | 4/1998 |

(56) References Cited

FOREIGN PATENT DOCUMENTS

| | | |
|---|---|---|
| EP | 0 882 955 A1 | 12/1998 |
| EP | 1 159 926 A2 | 12/2001 |
| EP | 1278007 | 1/2003 |
| EP | 1524719 A1 | 4/2005 |
| EP | 1 810 627 A1 | 7/2007 |
| EP | 2264828 A1 | 12/2010 |
| EP | 2468359 A1 | 6/2012 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | H07185019 A | 7/1995 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | H09164215 A | 6/1997 |
| JP | H1099455 A | 4/1998 |
| JP | 11244298 A | 9/1999 |
| JP | 2000324840 A | 11/2000 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| JP | 2011024203 A | 2/2011 |
| KR | 20070093068 A | 9/2007 |
| KR | 20100014406 A | 2/2010 |
| KR | 20120055063 A | 5/2012 |
| SU | 166452 | 11/1964 |
| SU | 401367 A1 | 10/1973 |
| SU | 727201 A2 | 4/1980 |
| WO | 97/41924 A1 | 11/1997 |
| WO | 97/43971 A2 | 11/1997 |
| WO | 9925248 A1 | 5/1999 |
| WO | 00/36985 A2 | 6/2000 |
| WO | 00/48672 A1 | 8/2000 |
| WO | 00/51513 A1 | 9/2000 |
| WO | 01/01847 | 1/2001 |
| WO | 01/74252 A2 | 10/2001 |
| WO | 02/45790 A2 | 6/2002 |
| WO | 02/061880 A2 | 8/2002 |
| WO | 2004/112628 A1 | 12/2004 |
| WO | 2005/016119 A2 | 2/2005 |
| WO | 2008002517 A1 | 1/2008 |
| WO | 2010/035831 A1 | 4/2010 |

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report EP 12003728.8 dated Jul. 18, 2012.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94In Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.

(56) References Cited

OTHER PUBLICATIONS

Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" in William RH, Rengachary SS (eds): Neurosurgery, New York: McGraw.cndot.Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 elated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering; Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/ Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.

(56) References Cited

OTHER PUBLICATIONS

McLellan et al., "Vessel Sealing for Hemostasis During Pelvic Surgery" Int'l Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page; Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001)71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
S. Humphries Jr. et al., "Finite Element Codes to Model Electrical Heating and Non-Linear Thermal Transport in Biological Media", Proc. ASMA HTD-355, 131 (1997).
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
European Search Report EP 10006373 dated Oct. 11, 2010.
U.S. Appl. No. 08/136,098, filed Oct. 14, 1993; Roger A. Stern.
U.S. Appl. No. 08/483,742, filed Jun. 7, 1995; Roger A. Stern.
Goldberg et al. (1995) "Saline-enhanced RF Ablation: Demonstration of Efficacy and Optimization of Parameters", Radiology, 197(P): 140 (Abstr).
Humphries Jr. et al., "Finite-Element Codes to Model Electrical Heating and Non-Llnear Thermal Transport in Biological Media", Proc. ASME HTD-355, 131 (1997).
Johnson et al., "New Low-Profile Applicators for Local Heating of Tissues", IEEE Transactions on Biomedical Engineering, vol. BME-31, No. 1, Jan. 1984, pp. 28-37.
Solbiati et al. (1995) "Percutaneous US-guided RF Tissue Ablation of Liver Metastases: Long-term Follow-up", Radiology, pp. 195-203.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
Humphries Jr. et al., "Finite-Element Codes to Model Electrical Heating and Non-Linear Thermal Transport in Biological Media", Proc. ASME HTD-355, 131 (1997).
U.S. Appl. No. 14/011,414, filed Aug. 27, 2013, Ohri.
U.S. Appl. No. 14/011,438, filed Aug. 27, 2013, Ohri.
U.S. Appl. No. 08/136,098, filed Oct. 14, 1993, Roger A. Stern.
U.S. Appl. No. 08/483,742, filed Jun. 7, 1995, Roger A. Stern.
S. Humphries Jr. et al., "Finite Element Codes to Model Electrical Heating and Non-Linear Thermal Transport in Biological Media", Proc. ASME HTD-355, 131 (1997).
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.

(56) References Cited

OTHER PUBLICATIONS

European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
Japanese Office Action from JP Appl. No. 2012-107396 mailed Feb. 2, 2016.
Chinese Office Action from Chinese Appln. No. 201210205270.7 dated Apr. 23, 2015.
Decision of Rejection from Appl. No. JP 2012-107396 mailed Aug. 9, 2016.
Decision of Rejection from Japanese Application No. 2015-009601 mailed Jul. 26, 2016.

* cited by examiner

MICROWAVE ABLATION ANTENNA RADIATION DETECTOR

REFERENCE TO RELATED APPLICATIONS

The present application is a continuation application of U.S. patent application Ser. No. 14/048,835, filed on Oct. 8, 2013, which is a continuation application of U.S. patent application Ser. No. 12/487,917, filed on Jun. 19, 2009, now U.S. Pat. No. 8,552,915, the entire contents of each of which are incorporated by reference herein.

BACKGROUND

1. Technical Field

The present disclosure relates generally to microwave antennas. More particularly, the present disclosure is directed to radiation detectors for microwave ablation antennas.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole, in which microwave energy radiates perpendicularly from the axis of the conductor. A monopole antenna includes a single, elongated microwave conductor whereas a dipole antenna includes two conductors. In a dipole antenna, the conductors may be in a coaxial configuration including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide more effective outward radiation of energy. This type of microwave antenna construction is typically referred to as a "leaky waveguide" or "leaky coaxial" antenna.

Conventional microwave antennas operate at a single frequency allowing for creation of similarly shaped lesions (e.g., spherical, oblong, etc.). Some antennas are capable of radiating energy inside as well as outside tissue, due to well-tuned impedance matching. In some instances this may result in inadvertent radiation outside the tissue.

SUMMARY

According to one aspect of the disclosure, a radiation detector disposed on a microwave antenna assembly is disclosed. The radiation detector includes a receiving antenna adapted to receive errant microwave energy and a rectifier coupled to the receiving antenna that is adapted to rectify at least a portion of the errant microwave energy. A filter is coupled to the rectifier and is adapted to convert the rectified microwave energy into a detection signal.

According to another aspect of the present disclosure, a microwave antenna assembly is disclosed. The microwave assembly includes a hub adapted to couple the microwave antenna assembly to a microwave generator, a radiating section coupled to the hub through a feedline and a radiation detector disposed on the microwave antenna assembly proximally of the radiating section. The radiation detector includes a receiving antenna adapted to receive errant microwave energy, a rectifier coupled to the receiving antenna and being adapted to rectify at least a portion of the errant microwave energy and a filter coupled to the rectifier and adapted to convert the rectified microwave energy into a detection signal.

A method for detecting errant microwave energy is also contemplated by the present disclosure. The method includes an initial step of detecting errant microwave energy. The method also includes the steps of: rectifying at least a portion of the errant microwave energy through a rectifier coupled to the receiving antenna and filtering the rectified microwave energy through a filter coupled to the rectifier to convert the rectified microwave energy into a detection signal.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

The present disclosure provides for a radiation detector disposed on a microwave antenna. Generally, the detector is disposed in a location such that any unintended and/or errant radiation of microwave energy along the antenna is detected. The radiation detector converts the detected radiation into a detection signal, which is then transmitted to a control system (e.g., microwave generator) to either shut off the power supply and/or alert the user.

In one embodiment, the radiation detector includes a receiving antenna adapted to receive microwave energy radiating along the microwave antenna and a rectifying circuit including a rectifying device and a filter. The rectifying circuit rectifies the microwave energy incident on the receiving antenna into a sensing signal and then passes the sensing signal through the filter to the control system.

Figure 1:
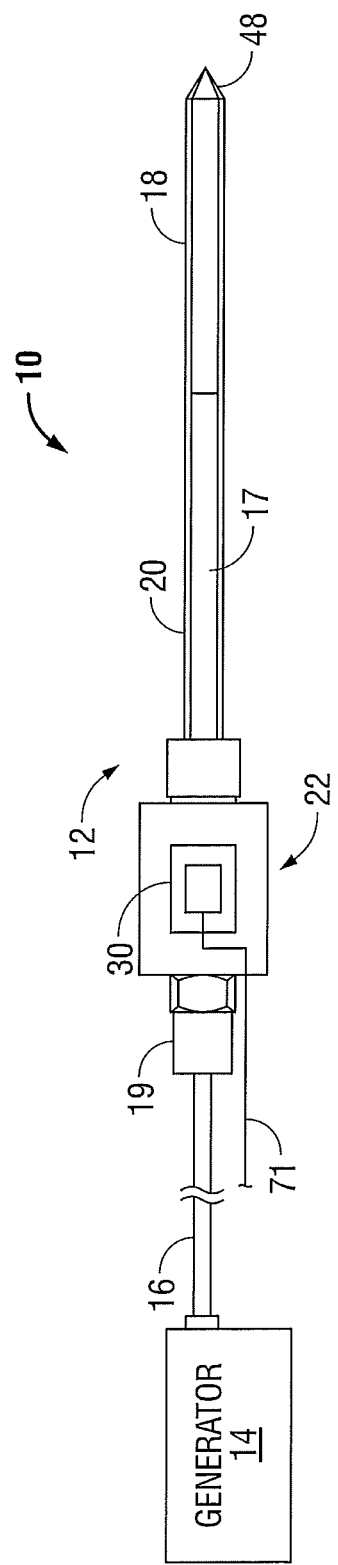
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 500 MHz to about 10,000 MHz. In the illustrated embodiment, the antenna assembly 12 includes a radiating section 18 connected by feedline 20 (or shaft) to the cable 16. More specifically, the feedline 20 is connected to a hub 22, which is connected to the cable 16 through a cable connector 19. The hub 22 may have a variety of suitable shapes, e.g., cylindrical, rectangular, etc.

The feedline 20 may be coaxial and include an inner conductor surrounded by an inner insulator, which is, in turn, surrounded by an outer conductor 17 (e.g., a cylindrical conducting sheath). The inner conductor and outer conductor 17 may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the feedline 20 may be formed from a coaxial, semi-rigid or flexible cable having a wire with a 0.047" outer diameter rated for 50 Ohms.

Figure 2:
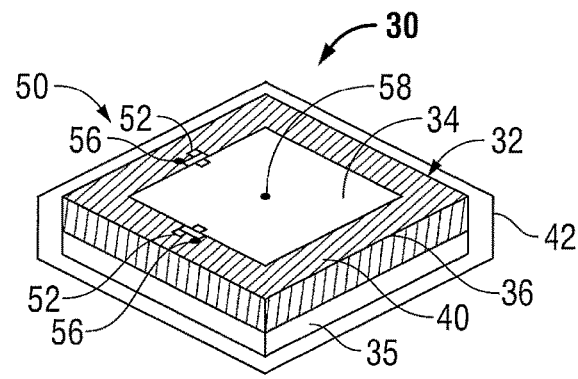
FIG. 2 is a perspective view of a radiation detector according to one embodiment of the present disclosure.

The antenna assembly 12 includes a radiation detector 30 disposed proximally relative to the radiating section 18, e.g., on the outer surface of the hub 22. With reference to FIGS. 2-5, the radiation detector 30 includes a so-called square "patch" receiving antenna 32 formed as a top antenna member 34 and a lower grounding member 35. The antenna member 34 is shaped as a square patch and is disposed on a top surface 40 of the substrate 36 as shown in FIGS. 2, 3 and 5.

The grounding member 35 is formed as a border frame patch and is disposed on a bottom surface 41 of the substrate 36 as shown in FIGS. 2, 4 and 5. The square shape of the receiving antenna 32 allows the radiation detector 30 to act as a 360° receiver, allowing the radiation detector 30 to detect microwave radiation from any direction. In one embodiment, each side of the receiving antenna 32 may be substantially n $\lambda$/4 of the wavelength of the microwave energy being supplied to the antenna 12, where n is an integer, hence, the side may be $\lambda$/4, $\lambda$/2, $\lambda$, etc.

Figure 5A:
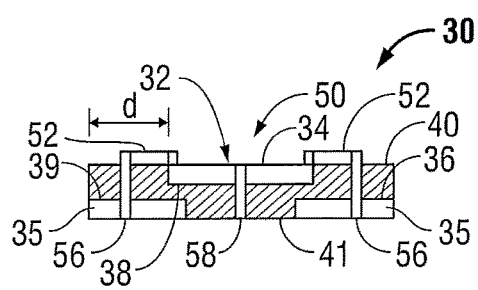
FIGS. 5A-B are cross-sectional, side view of the radiation detector of FIG. 2.

As best shown in FIG. 5A, the substrate 36 includes a top depression 38 on the top surface 40 thereof. The depression 38 is dimensioned such that the antenna member 34 fits therein and that the antenna member 34 is substantially flush with the top surface 40. The substrate 36 also includes a bottom depression 39 on the bottom surface 41 thereof. The bottom depression 39 is shaped as a border frame around the periphery of the substrate 36. The depression 39 is also dimensioned such that the grounding member 35 fits therein and the grounding member 35 is substantially flush with the bottom surface 41. The top and bottom depressions 38 and 39 may be formed a distance d from the perimeter of the substrate 36, such that when disassembled, the antenna member 34 fits within the grounding member 35.

Figure 5B:
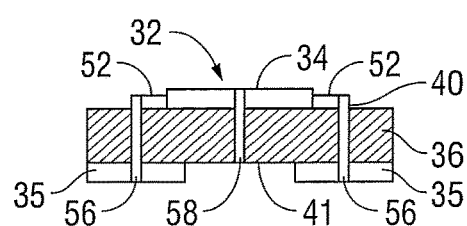

In another embodiment, as shown in FIG. 5B, the substrate 36 may have a planar top surface 40 and a planar bottom surface 41 with the antenna and grounding members 34 and 35 disposed thereon.

In one embodiment, the substrate 36 may be formed from a non-conductive conformal material such as polyesters, polyimides, polyamides, polyamide-imides, polyetherimides, polyacrylates, polyethylene terephthalate, polyethylene, polypropylene, polyvinylidene chloride, polysiloxanes, combinations thereof and the like. The antenna and grounding members 34 and 35 may be formed from a conformal sheet of conductive material such as copper, gold, stainless steel or other conductive metals with similar conductivity values. In one embodiment, the receiving antenna 32 may be plated with other materials, e.g., other conductive materials, to improve the conductive properties thereof. The conformal nature of the substrate 36 and the receiving antenna 32 allows the radiation detector 30 to be disposed on the hub 22 of any suitable shape (e.g., cylindrical). Thus, the radiation detector 30 may be wrapped around the hub 22. The radiation detector 30 may also be encased in a shell 42 (e.g., epoxy) to provide for sterilization compatibility. The encasement may be accomplished once the radiation detector 30 is conformed to the hub 22.

With continued reference to FIGS. 2-5, the radiation detector 30 also includes a rectifying circuit 50 including one or more rectifiers 52 (FIGS. 2 and 3) and a filter 54 (FIG. 4). The rectifiers 52 are electrically coupled to the antenna member 34. The rectifiers 52 also include a shunt connection 56 passing through the substrate 36 to the grounding member 35 as best shown in FIG. 5. In addition, the radiation detector 30 includes a center tap feed 58 coupling the antenna member 34 to the grounding member 35. The center tap feed 58 passes through the substrate 36 in a similar manner as the shunt connections 56. The center tap feed 58 and the shunt connections 56 provide the only electrical connectivity between the antenna and grounding members 34 and 35, which are otherwise electrically insulated by the substrate 36.

The center tap feed 58 may be placed at a location of high current density and low electric field density to optimize DC current harvesting and minimize RF current disturbance. In other words, the center tap feed 58 may be placed in a location of low RF impedance. Rectifiers 52 are placed in locations of high electric field density and low current density.

Figure 3A:
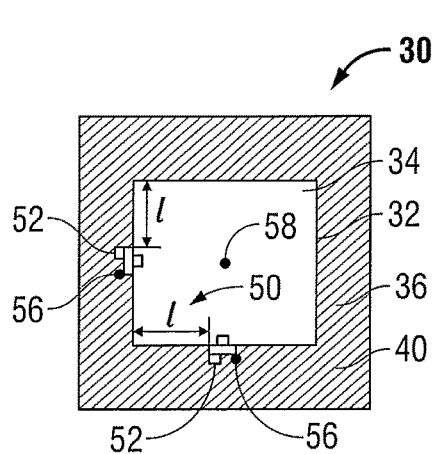
FIGS. 3A-B are top views of the radiation detector of FIG. 2.
Figure 3B:
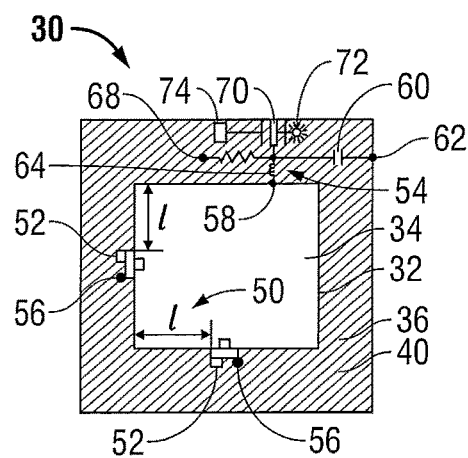

The rectifiers 52 may be any type of suitable diodes such as Zener diode, Schottky diode, tunnel diode and the like. The rectifiers 52 may be in direct contact with the antenna member 34 or through an impedance matching network, which may include lumped elements and/or a transmission line. In addition, the rectifiers 52 may be disposed a predetermined distance/from the corner of the antenna member 34 (FIGS. 3A-B). The distance/may be varied to match the impedance of the rectifier 52 to the antenna assembly 12. The rectifiers 52 convert the sinusoidal shape of the microwave waveform by clipping the negative portion of the waveform. In other words, the rectifiers 52 clip the bottom portion of the sinusoid to rectify the microwave waveform.

Figure 4A:
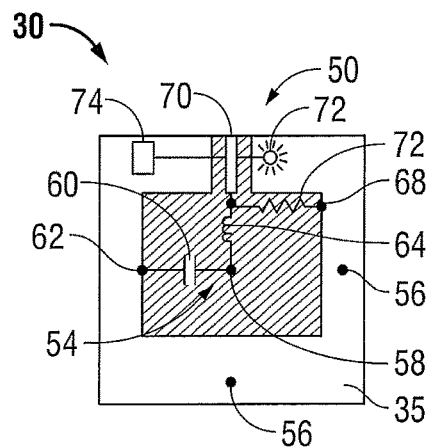
FIGS. 4A-B are bottom views of the radiation detector of FIG. 2.
Figure 4B:
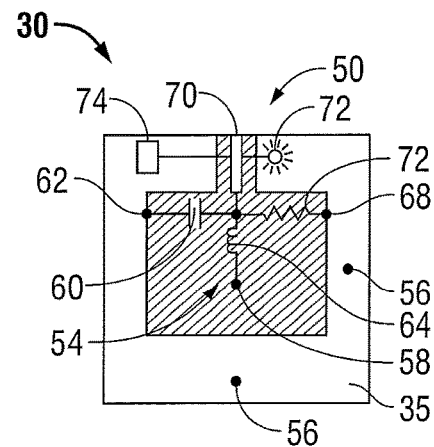

As shown in FIGS. 4A and B, the filter 54 is disposed at the bottom surface 41 and is electrically coupled to the center tap feed 58. The filter 54 may be an inductor-resistor-capacitor ("LRC") low pass filter that is adapted to convert the rectified sinusoidal waveform from the rectifiers 52 into a detection signal, which may be a DC voltage signal representative of the detected microwave radiation. The filter 54 includes a capacitor 60 coupled between the center tap feed 58 and a first shunt connection 62. The capacitor 60 is connected in series with an inductor 64, which is connected through a resistor 66 to a second shunt connection 68 as shown in FIG. 4A. In another embodiment, the capacitor 60, the inductor 64 and the resistor 66 may be coupled to each other in parallel as shown in FIG. 4B. The inductor 64 is coupled to the receiving antenna at the center tap feed 58, which is now disposed at the edge of the antenna member 34.

In a further embodiment, as shown in FIG. 3B, the filter 54 may be disposed on the top surface 40 and be coupled to antenna member 34 by the center tap feed 58. The first and second shunt connections 62 and 68 pass through the substrate 36 in a similar manner as the shunt connections 56.

The filter 54 is also connected to a voltage output 70 that may be coupled to a wire 71 (FIG. 1). The wire 71 may be disposed anywhere along the antenna assembly 12 such that the wire 71 has minimal effect on the radiation efficiency of the antenna assembly 12. When the filter 54 is configured as an LRC filter and connected to the voltage output 70, the filter 54 limits the microwave radiating from escaping through the wire 71 and allows the rectified DC current, namely, the detection signal to travel to the generator 14. A ground wire (not explicitly shown) is coupled to the grounding member 35 and provides the generator 14 with a reference signal for comparison of the detection signal therewith.

The detection signal may then be transmitted to the generator 14 or another control system, which compares the detection signal with a reference threshold signal. The reference signal may be preset to denote a threshold level indicative of dangerous levels of microwave radiation. If the generator 14 determines that the detection signal is above the reference signal, then the generator 14 may terminate or suspend the supply of energy to the antenna assembly 12 and/or alert the user. The generator 14 may include any suitable type of alert or alarm (e.g., audio, visual, etc.) that is activated when the detection signal is above the threshold.

In another embodiment, in addition to transmission of the detection signal to the generator 14, the detection signal may also be used to power any suitable alarm device, such as a light-emitting device (e.g., LED 72) disposed on the bottom surface 41. The LED 72 may be configured to operate above a predetermined threshold voltage. Thus, the detection signals above the threshold trigger the LED 72, indicates to the user that dangerous levels of microwave energy are emitted outside the radiating section 18. In another embodiment, an audible alarm (e.g., a speaker) may be used in place of the LED 72.

In a further embodiment, the radiation detector 30 may include a voltage limiting circuit 74 to ensure that the voltage level of the detection signal is regulated, such that, excessive voltage does not pass to the control circuitry of the generator 14. The voltage limiting circuit 74 may include a high impedance voltage buffer.

Figure 6:
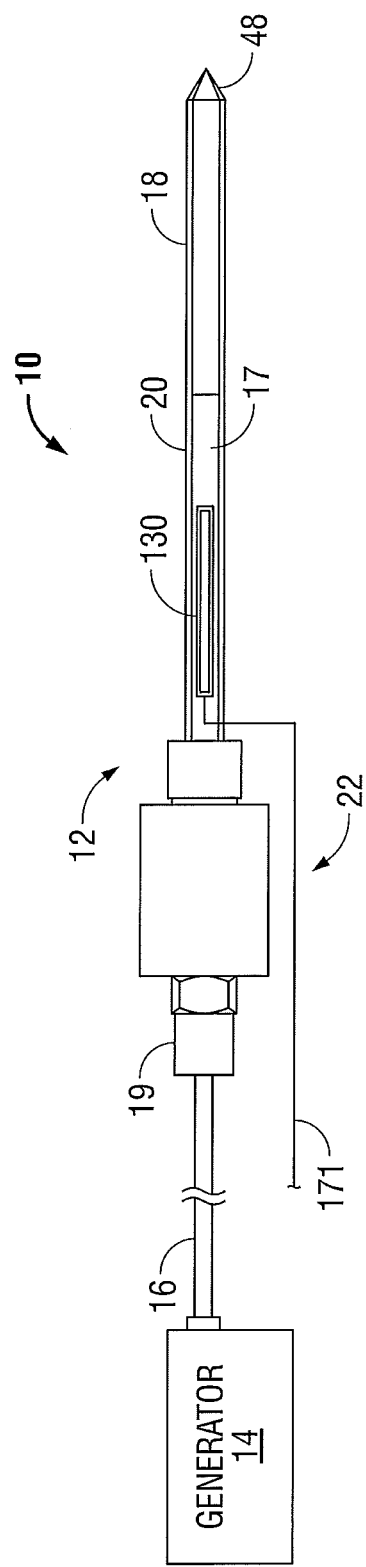
FIG. 6 is a schematic diagram of a microwave ablation system according to an embodiment of the present disclosure.
Figure 7:
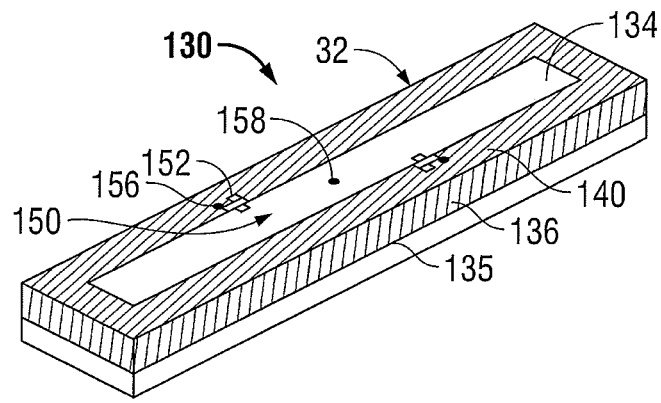
FIG. 7 is a perspective view of a radiation detector according to one embodiment of the present disclosure.

FIGS. 6-10 illustrate another embodiment of a radiation detector 130. With reference to FIGS. 7-10, the radiation detector 130 includes a linear receiving antenna 132 formed as a top antenna member 134 and a lower grounding member 135. The antenna member 134 is shaped as a rectangular patch and is disposed on a top surface 140 of the substrate 136 as shown in FIGS. 7-9. The linear receiving antenna 132 is disposed longitudinally on the antenna assembly 12, such that the longitudinal axis of the receiving antenna 132 is substantially parallel with the longitudinal axis of the antenna assembly 12. This configuration aligns the linear receiving antenna 132 with the emitted microwave energy.

In one embodiment, the grounding member 135 may be formed as a border frame patch and is disposed on a bottom surface 141 of the substrate 136 as shown in FIGS. 7, 9 and 10. In another embodiment, the outer conductor 17 may be used in lieu of the grounding member 135, such that the substrate 136 is disposed on top of the outer conductor 17.

Figure 10A:
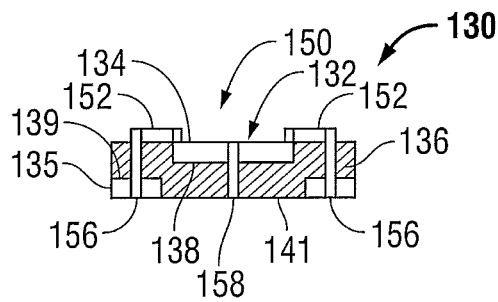
FIGS. 10A-B are cross-sectional, side view of the radiation detector of FIG. 7.

As best shown in FIG. 10A, the substrate 136 includes a top depression 138 on the top surface 40 thereof. The depression 138 is dimensioned such that the antenna member 134 fits therein and resides substantially flush with the top surface 140. If the grounding member 135 is utilized in a particular configuration, the substrate 136 will also be configured to include a bottom depression 139 on the bottom surface 141 thereof. The bottom depression 139 is shaped as a border frame around the periphery of the substrate 36. The depression 139 is dimensioned such that the grounding member 135 fits therein in a substantially flush orientation relative to the bottom surface 141.

Figure 10B:
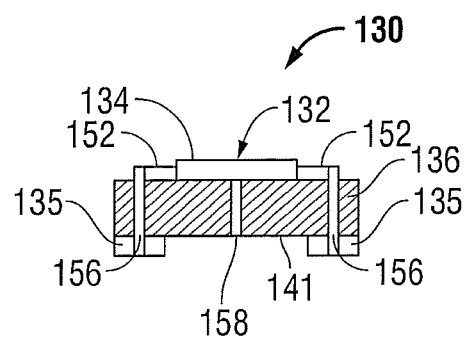

In another embodiment, as shown in FIG. 10B, the substrate 136 may have a planar top surface 140 and a planar bottom surface 141 with the antenna and grounding members 134 and 135 disposed thereon.

In one embodiment, the substrate 136 may be formed from the same non-conductive conformal materials as the substrate 36. The antenna and grounding members 134 and 135 may be formed from any suitable conformal conductive materials similar to the materials of the antenna and grounding members 134 and 135. The conformal nature of the substrate 136 and the receiving antenna 132 allows the radiation detector 130 to be disposed around the shaft of the outer conductor 17 (e.g., wrapped longitudinally thereabout).

With continued reference to FIGS. 7-10, the radiation detector 130 also includes a rectifying circuit 150 including one or more rectifiers 152 and a filter 154 (FIG. 9). The rectifiers 152 are electrically coupled to the antenna member 134 and include a shunt connection 156 passing through the substrate 136 to the grounding member 135 as best shown in FIG. 10. The radiation detector 130 also includes a center tap feed 158 coupling the antenna member 134 to the grounding member 135. In another embodiment, the shunt connections and the center tap feed 158 may shunt to the outer conductor 17.

Figure 8A:
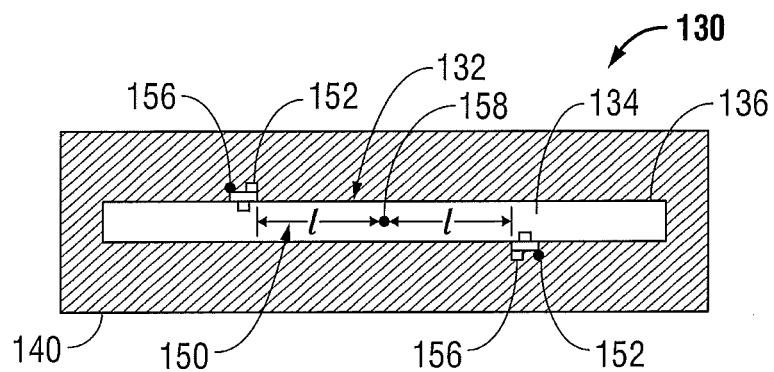
FIGS. 8A-B are top views of the radiation detector of FIG. 7.
Figure 8B:
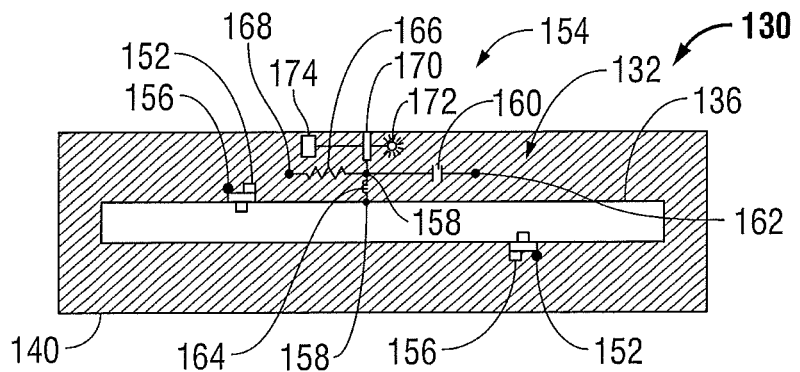
Figure 9A:
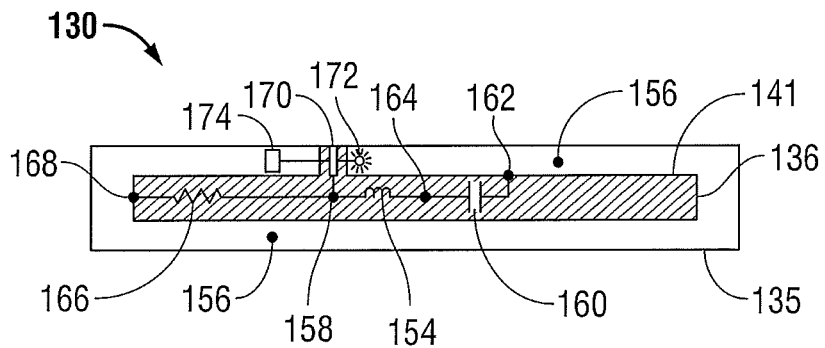
FIGS. 9A-B are bottom views of the radiation detector of FIG. 7.
Figure 9B:
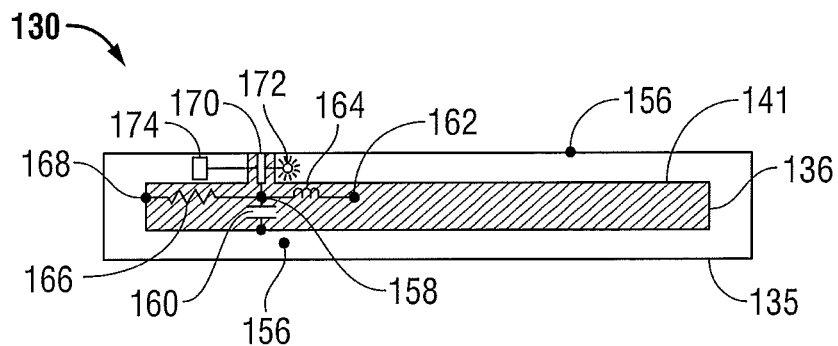

The rectifiers 152 may be disposed a predetermined distance/from center tap feed 158 (FIGS. 8A-B). The distance/may be varied to match the impedance of the rectifier 152 to the antenna assembly 12. As shown in FIG. 9, the filter 154 is disposed at the bottom surface 141 and is electrically coupled to the center tap feed 158. The filter 154 is an LRC low pass filter that is adapted to convert the rectified sinusoidal waveform from the rectifiers 152 into a detection signal. The filter 154 is also connected to a voltage output 170 which may be coupled to a wire 171 (FIG. 6). A ground wire (not explicitly shown) is coupled to the grounding member 135 and provide the generator 14 with a reference signal for comparison of the detection signal therewith. The filter 154 is coupled to the center tap feed 158 and first and second shunt connections 162 and 168. The filter 154 also includes a capacitor 160, an inductor 164 and a resistor 166 coupled in series as shown in FIG. 9A. In another embodiment, the capacitor 160, the inductor 164 and the resistor 166 may be coupled to each other in parallel as shown in FIG. 9B.

In a further embodiment, as shown in FIG. 8B, the filter 154 may be disposed on the top surface 140 and be coupled to antenna member 134 by the center tap feed 158. The first and second shunt connections 162 and 168 pass through the substrate 136 in a similar manner as the shunt connection 156.

The detection signal may then be transmitted to the generator 14 or another control system, which compares the detection signal with a reference signal in the manner discussed above. In another embodiment, the radiation detector 130 also includes an LED 172 coupled to the voltage output 170. The LED 172 lights up when the detection signal is above a predetermined threshold voltage. In a further embodiment, the radiation detector 130 may also include a voltage limiting circuit 174 to ensure that excessive voltage does not pass to the control circuitry of the generator 14.

The present disclosure provides for a radiation detector that allows for microwave ablation systems to recognize unintended radiation of microwave energy along the antenna assembly 12 toward the user. This is particularly useful for dielectrically buffered antennas that continue to radiate microwave energy efficiently, regardless of the radiating environment (e.g., inside or outside tissue). Thus, if the antenna assembly 12 is energized while in open air, the radiation detector 30 senses a high level of microwave radiating along the antenna assembly 12 and then transmits a detection signal to the generator 14, which then registers the error and suspends the supply of power.

Figure 11:
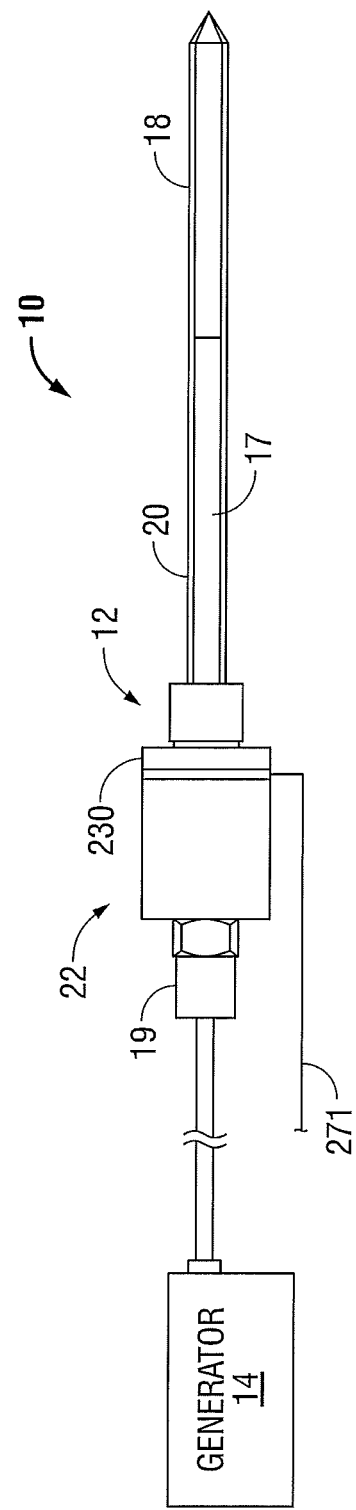
FIG. 11 is a schematic diagram of a microwave ablation system according to an embodiment of the present disclosure.
Figure 12:
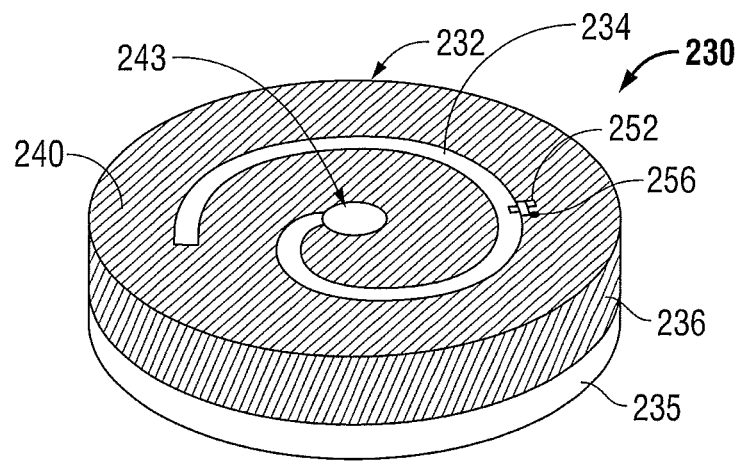
FIG. 12 is a perspective view of a radiation detector according to one embodiment of the present disclosure.
Figure 13:
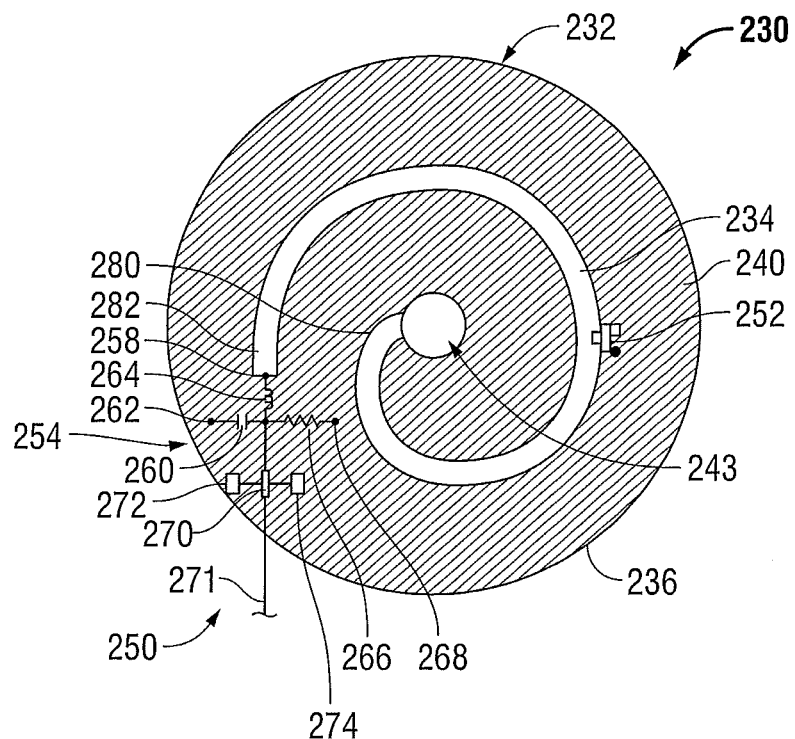
FIG. 13 is a top view of the radiation detector of FIG. 12.
Figure 14:
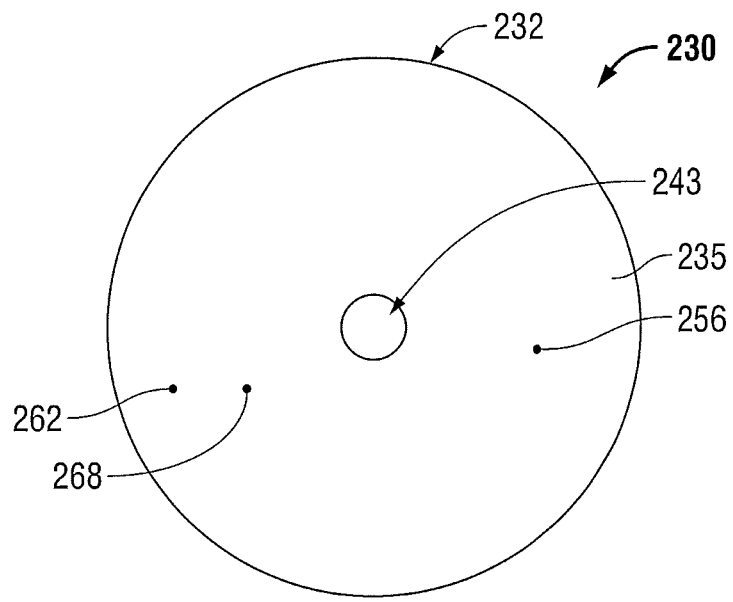
FIG. 14 is a bottom view of the radiation detector of FIG. 12.

FIGS. 11-14 illustrate another embodiment of a radiation detector 230. With reference to FIGS. 12-14, the radiation detector 230 includes a circular receiving antenna 232 formed as a spiral antenna member 234 and a grounding member 235. The circular receiving antenna 232 includes an aperture 243 defined therethrough for insertion around the feedline 20. The aperture 243 allows the circular receiving antenna 232 to be disposed transversely with respect to a longitudinal axis defined by the antenna assembly 12. This configuration aligns the circular receiving antenna 232 with the emitted microwave energy. The antenna member 234 has a spiral shape and is disposed on a top surface 240 of a substrate 236 as shown in FIGS. 12 and 13. The antenna member 234 includes an inner end 280 coupled to the aperture 243 and an outside end 282 (FIG. 13).

In one embodiment, the grounding member 235 may be formed as a solid circular patch and is disposed on a bottom surface 241 of the substrate 236 as shown in FIGS. 12 and 14. The substrate 236 may be formed from the same non-conductive conformal materials as the substrate 36. The antenna and grounding members 234 and 235 may be formed from any suitable conformal conductive materials similar to the materials of the antenna and grounding members 34 and 35.

With reference to FIG. 13, the radiation detector 230 also includes a rectifying circuit 250 including one or more rectifiers 252 and a filter 254. The rectifier 252 is electrically coupled to the antenna member 234 and includes a shunt connection 256 passing through the substrate 236 to the grounding member 235 as shown in FIGS. 12 and 14. The radiation detector 230 also includes a center tap feed 258 (FIG. 13). The center tap feed 258 may be placed at a location of high current density and low electric field density to optimize DC current harvesting and minimize RF current disturbance, such as the outside end 282. In other words, the center tap feed 258 may be placed in a location of low RF impedance. Rectifiers 252 are placed in locations of high electric field density and low current density.

As shown in FIG. 13, the filter 254 is disposed on the top surface 240 and is coupled to antenna member 234 by the center tap feed 258. The filter 254 is an LRC low pass filter that is adapted to convert the rectified sinusoidal waveform from the rectifiers 252 into a detection signal. The filter 254 is also connected to a voltage output 270 which may be coupled to a wire 271 (FIG. 11). A ground wire (not explicitly shown) is coupled to the grounding member 235 and provides the generator 14 with a reference signal for comparison of the detection signal.

The filter 254 is coupled to the center tap feed 258 and first and second shunt connections 262 and 268. The filter 254 also includes a capacitor 260, an inductor 264 and a resistor 266 coupled in series. In another embodiment, the capacitor 260, the inductor 264 and the resistor 266 may be coupled to each other in parallel. The first and second shunt connections 262 and 268 pass through the substrate 236 in a similar manner as the center tap feed 258.

The detection signal may then be transmitted to the generator 14 or another control system, which compares the detection signal with a reference signal in the manner discussed above. In another embodiment, the radiation detector 230 also includes an LED 272 coupled to the voltage output 270. The LED 272 lights up when the detection signal is above a predetermined threshold voltage. In a further embodiment, the radiation detector 230 may also include a voltage limiting circuit 274 to ensure that excessive voltage does not pass to the control circuitry of the generator 14.

Figure 15:
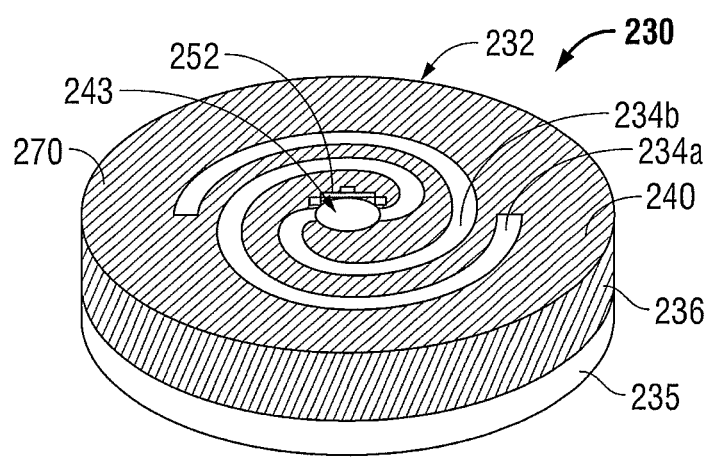
FIG. 15 is a perspective view of a radiation detector according to one embodiment of the present disclosure.
Figure 16:
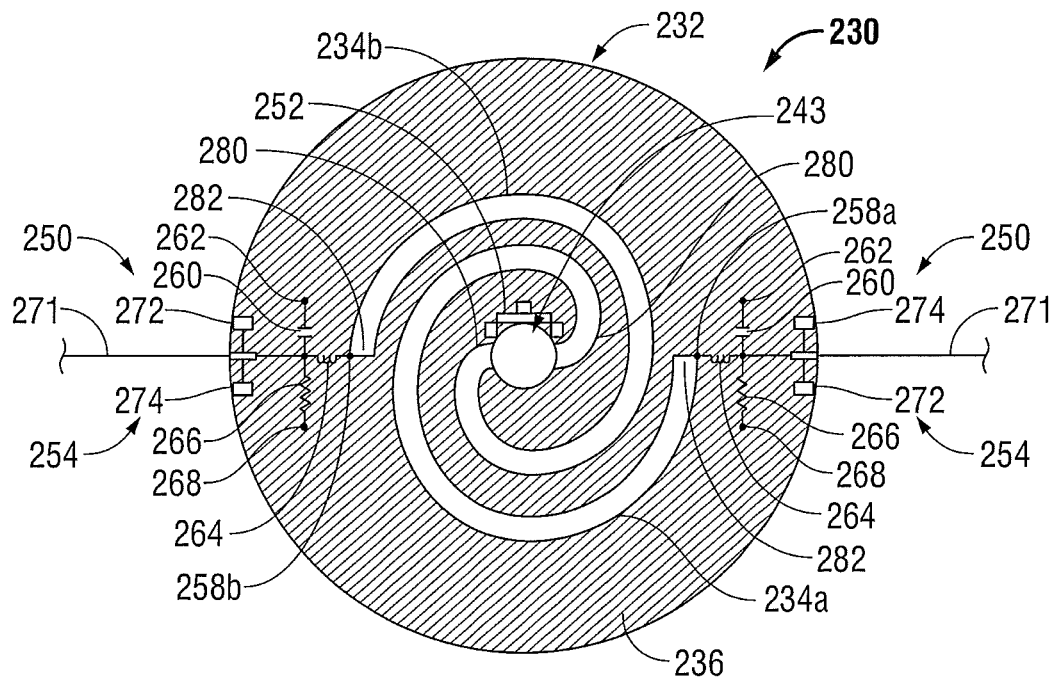
FIG. 16 is a top view of the radiation detector of FIG. 15.
Figure 17:
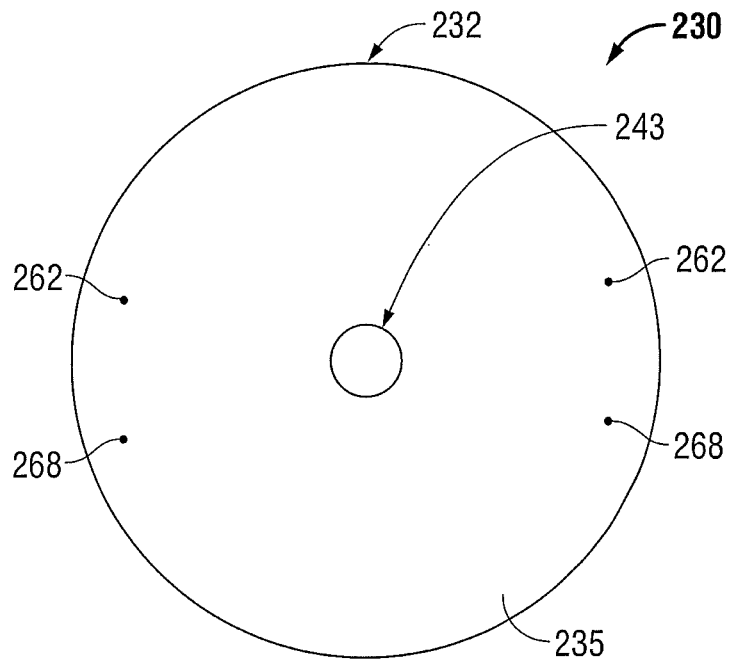
FIG. 17 is a bottom view of the radiation detector of FIG. 15.

FIGS. 15-17 illustrate another embodiment of a radiation detector 230 which includes a circular receiving antenna 232 formed as a two top antenna members 234a and 234b and a lower grounding member 235. The circular receiving antenna 232 includes an aperture 243 defined therethrough for insertion around the feedline 20. The aperture 243 allows the circular receiving antenna 232 to be disposed transversely with respect to a longitudinal axis defined by the antenna assembly 12. This configuration aligns the circular receiving antenna 232 with the emitted microwave energy. The antenna members 234a and 234b have a spiral shape and are disposed on a top surface 240 of the substrate 236 as shown in FIGS. 15 and 16. Each of the antenna members 234a and 234b includes an inner end 280 coupled to the aperture 243 and an outside end 282.

In one embodiment, the grounding member 235 may be formed as a solid circular patch and is disposed on a bottom surface 241 of the substrate 236 as shown in FIGS. 16 and 17. The substrate 236 may be formed from the same non-conductive conformal materials as the substrate 36. The antenna members 234a and 234b and grounding member 235 may be formed from any suitable conformal conductive materials similar to the materials of the antenna and grounding members 34 and 35.

With reference to FIG. 16, the radiation detector 230 also includes a rectifying circuit 250 including one or more rectifiers 252 and filters 254. The rectifier 252 electrically couples the antenna members 234a and 234 at the inner ends 280. This location coincides with high electric field density and low current density. The radiation detector 230 also includes center tap feeds 258a and 258b (FIG. 16). The center tap feeds 258a and 258b may be placed at a location of high current density and low electric field density to optimize DC current harvesting and minimize RF current disturbance, such as the outside end 282 of the antenna member 234. In other words, the center tap feeds 258a and 258b may be placed in a location of low RF impedance.

As shown in FIG. 14, the filters 254 are disposed on the top surface 240 and are coupled to antenna members 234a and 234b, respectively, at the center tap feeds 258a and 258b. The filters 254 are LRC low pass filters adapted to convert the rectified sinusoidal waveform from the rectifier 252 into a detection signal. The filters 254 are also connected to respective voltage outputs 270 which may be coupled to the wire 271 (FIG. 11). The signals from the filters 254 provide the generator 14 with detection signals, which the generator 14 then processes to determine the amount of radiation.

Each of the filters 254 is coupled to first and second shunt connections 262 and 268. Each of the filters 254 also includes a capacitor 260, an inductor 264 and a resistor 266 coupled in series. In another embodiment, the capacitor 260, the inductor 264 and the resistor 266 may be coupled to each other in parallel. The first and second shunt connections 262 and 268 pass through the substrate 236 in a similar manner as the shunt connection 256.

The detection signal may then be transmitted to the generator 14 or another control system, which compares the detection signals in the manner discussed above. In another embodiment, the radiation detector 230 also includes an LED 272 coupled to the voltage output 270 of each of the filters 254. The LEDs 272 light up when the detection signal is above a predetermined threshold voltage. In a further embodiment, the radiation detector 230 may also include a voltage limiting circuit 274 coupled to each of the filters 254 to ensure that excessive voltage does not pass to the control circuitry of the generator 14.

Figure 18:
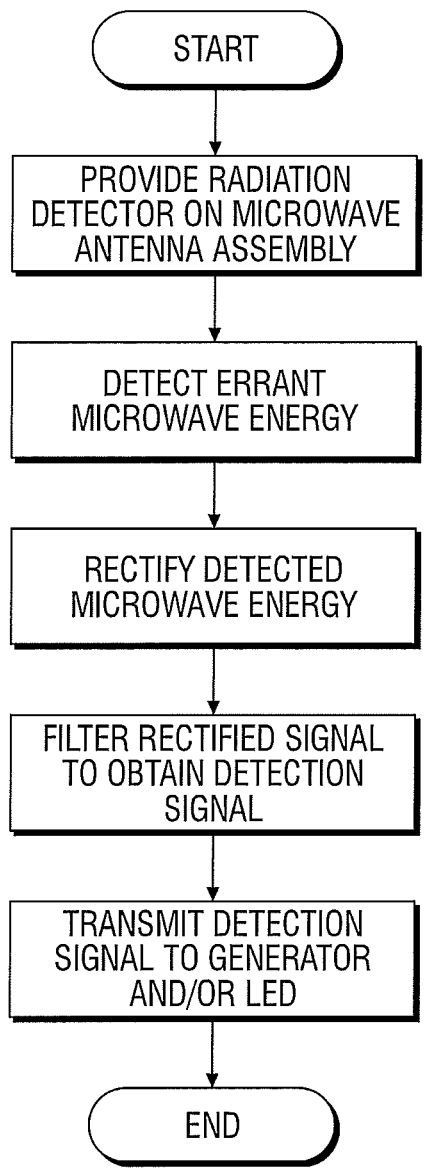
FIG. 18 is a flow chart of a method according to the present disclosure.

FIG. 18 shows a method for detecting errant microwave energy outside the radiating section 18. The method of the present disclosure is described with reference to the radiation detector 30. It should be appreciated that the method may be practiced with other radiation detectors, such as the radiation detectors 130, 230 and the like. The method includes an initial step of providing the radiating detector 30 on the microwave antenna assembly 12 which includes wrapping the radiating section 30 on the hub 22. The method may also include the step of connecting the radiation detector 30 to the generator 14 or another control system.

During operation, any errant microwave radiation outside the desired emission area, such as outside the radiating section 18, is picked up by the receiving antenna 32, namely, the antenna member 34. The detected microwave energy is then rectified by the rectifiers 52 and the rectified signal is filtered by the filter 54 into a detection signal (e.g., a DC voltage signal). The detection signal is then used to light up the LED 72 and/or is transmitted to generator 14. The generator 14 compares the detection signal to a threshold value to determine whether the level of the microwave energy is unsafe. If the determination is made that the level of microwave energy is excessive, the generator 14 may either suspend the supply of microwave energy and/or alert the user of this occurrence.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A method for detecting microwave energy, the method comprising:
   receiving microwave energy at a receiving antenna coupled to a microwave antenna assembly;
   rectifying at least a portion of the microwave energy through a rectifier coupled to the receiving antenna;
   filtering the rectified microwave energy through a filter coupled to the rectifier to convert the rectified microwave energy into a detection signal, wherein the filter includes a capacitor, an inductor, and a resistor coupled in series or parallel;
   comparing the detection signal with a predetermined threshold signal; and
   suspending supply of microwave energy based on the comparison of the detection signal with the predetermined threshold signal.

2. The method according to claim 1, further comprising:
   providing an alert based on the comparison of the detection signal with a predetermined threshold signal.

3. The method according to claim 1, further comprising:
   energizing a light-emitting device coupled to the filter, the light-emitting device adapted to operate when the detection signal is above the predetermined threshold signal.

4. The method according to claim 1, further comprising:
   transmitting the detection signal to a generator coupled to the microwave antenna assembly.

5. The method according to claim 4, further comprising:
   comparing the detection signal with a reference signal, wherein a ground wire is configured to provide the reference signal to the generator; and
   suspending supply of microwave energy based on the comparison of the detection signal with the reference signal.

6. The method of claim 5, further comprising:
   adjusting a voltage level of the detection signal with a voltage limiting circuit, the voltage limiting circuit includes a high impedance voltage buffer.

7. A method for detecting microwave energy, the method comprising:
   receiving microwave energy at a receiving antenna coupled to a microwave antenna assembly;
   rectifying at least a portion of the microwave energy through a rectifier coupled to the receiving antenna;
   filtering the rectified microwave energy through a filter coupled to the rectifier to convert the rectified microwave energy into a detection signal, wherein the filter includes a capacitor, an inductor and a resistor coupled in series or parallel; and
   indicating through an indicator coupled to the filter that the detection signal exceeds a predetermined threshold, wherein the indicator is a light-emitting device powered by the detection signal.

8. The method according to claim 7, wherein the indicator is an audible alarm.

9. A method for detecting microwave energy, the method comprising:
   receiving microwave energy at a receiving antenna coupled to a microwave antenna assembly;

rectifying at least a portion of the microwave energy through a rectifier coupled to the receiving antenna;

filtering the rectified microwave energy through a filter coupled to the rectifier to convert the rectified microwave energy into a detection signal, wherein the filter includes a capacitor, an inductor, and a resistor coupled in series or parallel; and transmitting the detection signal to a generator coupled to the microwave antenna assembly.

10. The method according to claim 9, further comprising:

comparing the detection signal with a reference signal, wherein a ground wire is configured to provide the reference signal to the generator; and suspending supply of microwave energy based on the comparison of the detection signal with the reference signal.

11. The method of claim 10, further comprising:

adjusting a voltage level of the detection signal with a voltage limiting circuit, the voltage limiting circuit includes a high impedance voltage buffer.

* * * * *